United States Patent [19]

Ezzell et al.

[11] 4,337,211
[45] Jun. 29, 1982

[54] FLUOROCARBON ETHERS HAVING SUBSTITUTED HALOGEN SITE(S) AND PROCESS TO PREPARE

[75] Inventors: Bobby R. Ezzell, Lake Jackson; William P. Carl, Angleton; William A. Mod, Lake Jackson, all of Tex.

[73] Assignee: The Dow Chemical Company, Midland, Mich.

[21] Appl. No.: 158,428

[22] Filed: Jun. 11, 1980

[51] Int. Cl.$^3$ .................... C07C 69/67; C07C 143/70
[52] U.S. Cl. .............................. 260/456 F; 260/465.4; 260/501.15; 260/502.4 R; 260/502.5; 260/513 F; 260/543 R; 260/543 F; 260/543 P; 260/544 F; 260/544 Y; 260/950; 560/150; 560/170; 560/180; 560/184; 567/567; 567/581; 567/583; 567/586; 564/14; 564/96; 564/120
[58] Field of Search ........... 260/456 R, 456 F, 501.15, 260/465.4, 502.4 R, 502.5, 513 F, 513 N, 543 R, 543 F, 543 P, 544 F, 544 Y, 950, 971; 560/150, 170, 180, 184; 562/581, 567, 583, 586; 564/14, 96, 160

[56] References Cited

U.S. PATENT DOCUMENTS

| | | | |
|---|---|---|---|
| 2,393,967 | 2/1946 | Brubaker | 526/195 |
| 2,559,752 | 7/1951 | Berry | 260/29.6 F |
| 2,593,583 | 4/1952 | Lontz | 528/502 |
| 3,041,317 | 6/1962 | Gibbs et al. | 526/243 |
| 3,114,778 | 12/1963 | Fritz et al. | 568/685 |
| 3,214,478 | 10/1965 | Milian, Jr. | 568/615 |
| 3,242,218 | 3/1966 | Miller | 568/615 |
| 3,250,806 | 5/1966 | Warnell | 562/583 |
| 3,250,807 | 5/1966 | Fritz et al. | 560/184 |
| 3,282,875 | 11/1966 | Connolly et al. | 260/29.6 F |
| 3,301,893 | 1/1967 | Putnam et al. | 260/513 R |
| 3,450,684 | 6/1969 | Darby | 526/247 |
| 3,536,733 | 10/1970 | Carlson | 260/348.23 |
| 3,560,568 | 2/1971 | Resnick | 260/513 R |
| 3,654,245 | 4/1972 | Kometani et al. | 560/213 |
| 3,784,399 | 1/1974 | Grot | 428/213 |
| 3,909,378 | 9/1975 | Walmsley | 204/98 |
| 3,969,285 | 7/1976 | Grot | 521/32 |
| 4,025,405 | 5/1977 | Dotson | 204/98 |
| 4,032,866 | 6/1977 | Psarras et al. | 560/184 |
| 4,035,254 | 7/1977 | Gritzner | 204/98 |
| 4,035,255 | 7/1977 | Gritzner | 204/98 |
| 4,065,366 | 12/1977 | Oda et al. | 204/98 |
| 4,085,071 | 4/1978 | Resnick | 204/98 |
| 4,126,588 | 11/1978 | Ukihashi et al. | 521/31 |
| 4,138,426 | 2/1979 | England | 526/245 |
| 4,151,053 | 4/1979 | Seko et al. | 204/98 |
| 4,192,725 | 3/1980 | Dotson et al. | 204/98 |
| 4,197,179 | 4/1980 | Ezzell | 204/255 |

FOREIGN PATENT DOCUMENTS

| | | |
|---|---|---|
| 52-118597 | of 1977 | Japan. |
| 54-52690 | 4/1979 | Japan. |
| 1406673 | 9/1975 | United Kingdom. |
| 1497748 | 1/1978 | United Kingdom. |
| 1497749 | 1/1978 | United Kingdom. |
| 1518387 | 7/1978 | United Kingdom. |
| 2029827 | 3/1980 | United Kingdom. |

OTHER PUBLICATIONS

Derwent Alerting Bulletin and Country Order, vol. 7, No. 20, Apr. 13, 1967, Abstract of German 1,238,458.
Hudlicky, M. "Chemistry of Organic Fluorine Compounds" 2nd Ed. John Wiley & Sons, Publ. (1976) pp. 20, 21.
Fearn, James E. et al. *Journal of Polymer Science*, vol. 4, pp. 131-140. (1966).
Lovelace, Rausch and Postelnek, "Aliphatic Fluorine Compounds" Reinhold publ. (1958) p. 107.
Chambers, R. D. "Fluorine in Organic Chemistry" John Wiley & Sons, Publ. (1973) pp. 211-212.
Evans, F. W. et al. *Journal of Organic Chemistry* vol. 33, pp. 1837-1839, May 1968.
Seko, Maomi, "Commercial Operation of the Ion Exchange Membrane Chlor-Alkali Process " presented to the ACS, Apr. 4-9, 1976.
Seko, Maomi, "The Asahi Chemical Membrane Chlaor-Alkali Process", Presented to the Chlorine Institute, Feb. 9, 1977.
Hora, C. J. et al. "Nafion Membranes Structured for High Efficiency Chlor-Alkali Cells" presented to the Electrochemical Society, Oct. 1977.
Olah, George A. *Aldrichimica Acta*, vol. 12, pp. 43-49, (1979).
Munn G. E., "Nafion Membranes-Factors Controlling Performance In the Electrolysis of Salt Solutions", presented to the Electrochemical Society, Oct. 1977.

*Primary Examiner*—Joseph E. Evans
*Assistant Examiner*—L. Hendriksen
*Attorney, Agent, or Firm*—James H. Dickerson, Jr.

[57] ABSTRACT

Novel perhalofluoro ethers and methods for preparing the same having generic formula,

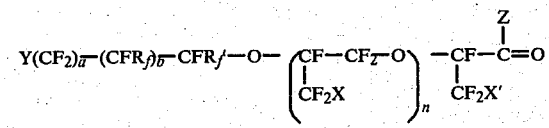

wherein
a=0 or an integer greater than O;
b=0 or an integer greater than O;
n=zero or an integer greater than zero;
R$_f$ and R'$_f$ are each independently selected from the group consisting of F, perfluoroalkyl and fluorochloroalkyl;
X=F, Cl or Br;
X'=Cl or Br;
Y is an acid group or a group easily convertible to an acid group;
Z=F, Cl, Br, OH, NRR' or OA;
R and R' are independently selected from the group consisting of hydrogen, an alkyl having one or more than one carbon atom and aryl;
A=alkali metal, quaternary nitrogen, or R.

17 Claims, No Drawings

FLUOROCARBON ETHERS HAVING SUBSTITUTED HALOGEN SITE(S) AND PROCESS TO PREPARE

BACKGROUND OF THE INVENTION

U.S. Pat. No. 3,301,893 teaches reacting

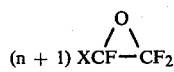

with

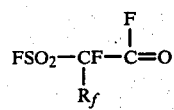

to form compounds represented by the general formula

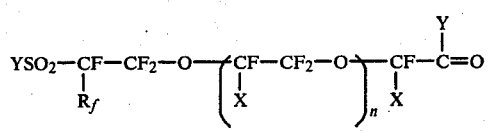

where
  $R_f$ is F or perfluoroalkyl radicals having from 1 to 10 carbon atoms;
  X is F or a trifluoromethyl radical, or mixtures thereof, where there is more than one X;
  Y is radical selected from the group consisting of fluorine, amino, hydroxyl and OMe radical where Me is a radical selected from the group consisting of the ammonium radical, alkali metals and other monovalent metals; and
  n is a number from 0 to 12.

U.S. Pat. No. 3,536,733 teaches the preparation of compounds represented by the general formula

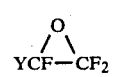

where Y is F or $CF_3$.

British Pat. No. 1,518,387 teaches the following reactions.

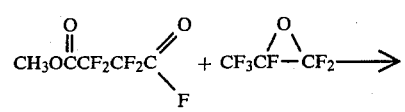

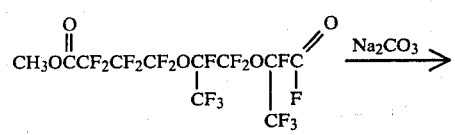

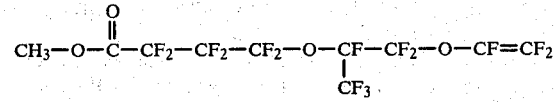

U.S. Pat. No. 3,282,875 teaches pyrolyzing compounds having the general formulas

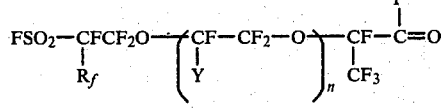

and

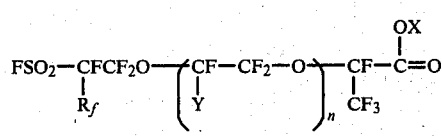

to form compounds represented by the general formula

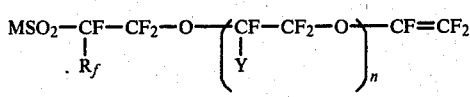

where
  $R_f$ is F or a perfluoroalkyl radical having from 1-10 carbon atoms;
  Y is F or a trifluoromethyl radical;
  n is an integer of 1-3, inclusive;
  M is F, hydroxyl radical, amino radical or OMe; and
  Me is an alkali metal or quaternary ammonium radical.
  X is alkali metal

BRIEF DESCRIPTION OF THE INVENTION

Novel compounds represented by the general formula

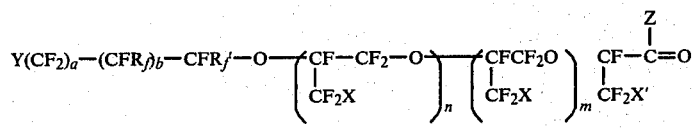

are prepared by reacting

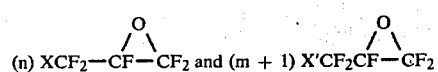

with

wherein
  a is 0 or an integer greater than 0;
  b is 0 or an integer greater than 0;
  m = zero or an integer greater than zero;
  n = zero or an integer grater than zero;

R′<sub>f</sub> and R<sub>f</sub> are independently selected from the group consisting of F, Cl, perfluoroalkyl and fluorochloroalkyl;

X=F, Cl, Br, or mixtures thereof when n>1;

X′ is independently Cl, Br, or mixtures thereof;

Y is an acid group or an acid derivative easily convertible to an acid group;

Z=F, Cl, Br, OH, NRR′ or OA;

R and R′ are independently selected from the group consisting of hydrogen, an alkyl having one or more than one carbon atom and an aryl;

A=alkali metal, quaternary ammonium, or R.

These compounds may be reacted to from various derivatives.

DETAILED DESCRIPTION OF THE INVENTION

The present invention relates to a novel class of fluorine containing ethers and methods for their preparation which ethers have terminal functionality according to the general formula:

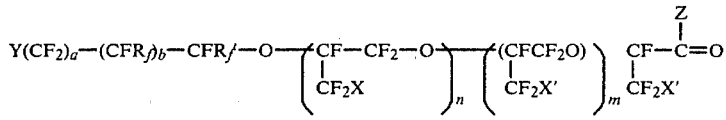

wherein a is 0 or an integer greater than 0;

b is 0 or an integer greater than 0;

m=zero or an integer greater than zero;

n=zero or an integer greater than zero;

R′<sub>f</sub> and R<sub>f</sub> are independently selected from the group consisting of F, Cl, perfluoroalkyl and fluorochloroalkyl;

X=F, Cl, Br, or mixtures thereof when n>1;

X′=Cl, Br, or mixtures thereof when m>1;

Y is an acid group or an acid derivative easily convertible to an acid group;

Z=F, Cl, Br, OH, NRR′ or OA;

R and R′ are independently selected from the group consisting of hydrogen, an alkyl having one or more than one carbon atoms, and aryl; and A=alkali metal, quaternary ammonium, or R.

These compounds are intermediates which may be further reacted to form a novel class of monomers, which, in turn, may then be polymerized and used in the preparation of chemically stable ion exchange resins or membranes.

Y is an acid group or an acid derivative easily convertible to an acid group. Y may be SO<sub>2</sub>-Z,

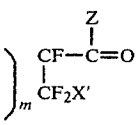

or C≡N or other appropriate groups (as Z is defined above).

When the polymers ultimately derived from these intermediates are to be formed into sheets for use as membranes such as in chlor-alkali cells, it is desirable to choose Z so that the polymers formed are thermoplastic to allow fabrication by conventional means, such as melt extrusion. After fabrication they can be easily converted to the acid or alkali metal salt of the acid. As an example, when Y=SO<sub>2</sub>F (Z=F), the intermediate is converted to an olefin monomer still having the —SO<sub>2</sub>F group. The monomer is then copolymerized to form a polymer containing the SO<sub>2</sub>F group that can be formed into sheets by various plastic fabrication techniques. After fabrication, the SO<sub>2</sub>F group is easily converted to the alkali metal salt of the corresponding sulfonic acid, —SO<sub>2</sub>ONa (Z=ONa), which can be converted to the sulfonic acid, —SO<sub>2</sub>OH (Z=OH), by reaction with acids, such as mineral acids.

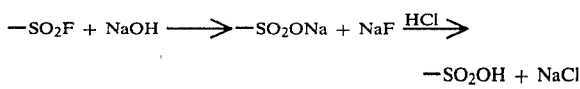

When Y is chosen as —C≡N, a nitrile, the above conditions are met since it is well known that nitriles are converted to carboxylic acids by hydrolysis.

When the polymers derived from the olefins from the present intermediates are to be used in particle or powder form, such as for acid catalyst, it is not critical in the choice of Z since fabrication is not as large a factor. In this case, Z can conveniently be any of the radicals listed. It can be —OH so as to directly have Y as an acid group or it can be any group rendering Y convertable to an acid group by further reaction.

X is chosen from the halogens Cl, Br or F, while X′ is chosen from Cl or Br. While iodine would also be useful for X or X′, formation of the ethers by the chemistry taught herein is hampered by side reactions causing low or nonexistent yields to the desired compounds.

When X′=Cl or Br and X=F, Cl or Br, new uses and novel and surprising new chemistry results from using the intermediates for additional chemical reactions. The prior art teaches that when Y=SO<sub>2</sub>F, n=0, m=O, and X′=F (U.S. Pat. No. 3,560,568) reaction of the intermediate with base does not produce the desired vinyl ether monomer, but rather a cyclic sulfone compound. Surprisingly, when n=0, m=O, Y=SO<sub>2</sub>F and X′=Cl or Br, reaction of the intermediate with base produces the desired vinyl ether product in one step. In addition to this benefit, choosing X or X′=Cl or Br in compounds where m or n>0 results in introducing a potential reaction site into polymers ultimately derived from monomers made from these intermediates. When m or n>0 both an acid site for ion exchange or catalyst (Y) and a reaction site for further reaction can be obtained by having X or X′=Cl or Br. In general, metallation reagents such as alkyl alkali metals can be used for reactions on these reaction sites.

There is additional benefit for having X′=Cl or Br. In this case it is helpful to have Cl or Br in this position for the subsequent reactions and uses for these compounds.

The variables in the structures have preferred values as follows: n=0–6, m=0–6, a=0–3, b=0–3. Even more preferred is n=0–3 and m=0–3. Even more preferably n=0 or 1 and m=0 or 1. Preferably X=Cl, X′=Cl and Y=Z′SO<sub>2</sub>. More preferably Y=Z′SO<sub>2</sub> and Z′=F. R<sub>f</sub> and R′<sub>f</sub> are preferably F.

In decarboxylations of the prior art, compounds of the terminal functionality shown below are common.

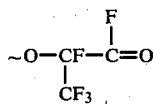

These materials generally require high temperatures and activators such as ZnO or silica to achieve reasonable yields to desired vinyl ethers.

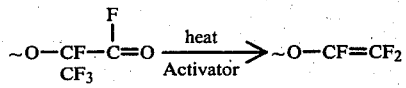

When X' is Cl or Br in the present invention, decarboxylation of these intermediates to vinyl ethers has been found to proceed under mild conditions and in excellent yields.

The novel class of compound of the present invention are conveniently prepared by reacting an acylfluoride or ketone of the general formula

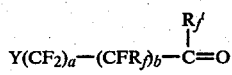

with perhalofluoro propylene epoxide of the formulas

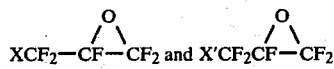

where Y, $R_f$, $R_f'$, a, b, X' and X are as defined above. The reactions are done in the presence of a fluoride ion yielding compound (MF-catalyst) at a temperature and a time sufficient to cause reaction, preferably at from below about $-20°$ C. to above about $50°$ C., in the liquid state, desirably in a liquid solvent for the intermediate fluoroalkoxide $Y(CF_2)_a - (CFR_f)_b - CFR_f'O^-M^+$ formed between the acid fluoride or ketone

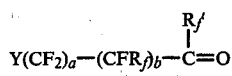

and the metal or ammonium fluoride fluorine ion yielding catalyst (MF). The reactions proceed generally according to the equation

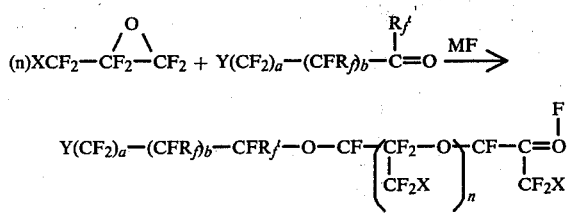

These acid fluoride intermediates can then be reacted with

to produce ethers having the general formula

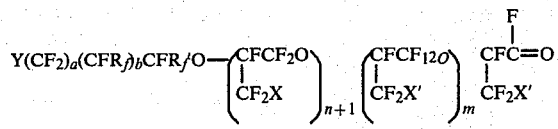

The latter reaction is preferable when X=F, and the intermediate is to be decarboxylated to a vinyl ether. When X=X'=Cl, Br, only the first reaction is necessary to form the desired compounds.

wherein
a is 0 or integer greater than 0;
b is 0 or integer greater than 0;
m=zero or an integer greater than zero;
n=zero or an integer greater than zero;
$R_f$ and $R_f'$ are independently selected from the group consisting of F, Cl, perfluoroalkyl and fluorochloroalkyl;
X=F, Cl or Br;
X'=Cl or Br;
Y is an acid group or an acid derivative easily convertible to an acid group;

Conversion of acid halides such as the acid fluorides described herein to carboxylic acids and derivatives by reaction with nucleophiles is well known to those skilled in the art. For example, conversion of the acid fluoride to the corresponding carboxylic acid is easily accomplished by reaction with water. Conversion to esters or amides is accomplished by reaction with alcohols or amines, respectively. The carboxylic acids (Z=OH) are easily converted to acid chlorides or bromides (Z=Cl, Br) by reaction with appropriate halogenation agents such as $PCl_5$ or $PBr_5$. Reactions of the carboxylic acid fluoride proceed according to the following equation:

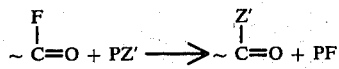

where
Z'=OH, NRR' or OR;
R and R' are independently selected from the group consisting of hydrogen, an alkyl having one or more than one carbon atom and aryl;
P is a cation or capable of forming a cation, such as Na+, K+, H+, etc. These reactions should be carried out for a time and at a temperature sufficient to form the products.

It is of course to be understood that in the reaction of the acid fluorides or ketones with the epoxides the ratio of reactants, the temperature of reaction, the amount of catalyst, as well as the amount and kind of solvent, influence the course, speed and direction of the reaction. Naturally the ratio of reactants bears more directly on the value of m and n in the generic formula than the other factors noted. For example, employing 1 or more moles of acid halide compound per mole of perhalofluoro epoxide results in a product rich in the n=0 product, i.e., greater than 1.5 n=0 to n=1, respectively and if the ratio is 2 to 1, respectively, the n=0 product, respectively, is about 92 to 1, respectively, whereas employing greater than 1 mole epoxide compound per mole of acid fluoride compound, i.e., 2 to 1, respectively, results in a product having a 3:9:1 ratio of n=2:n=1:n=0 products. The ratio of reactants thus can range, for practical purposes, from about 2 to 3 moles of the acylfluoride or ketone per mole of the halofluoro epoxide to 1 to 20 moles of the epoxide per mole of the acyl fluoride, the high acyl fluoride to epoxide producing predominantly the n=0 and the high epoxide to acyl fluoride producing the N2-12 ether, respectively, and mixtures thereof.

Solvents employed in accordance with the present invention should be nonreactive (e.g., do not contain hydroxyl groups) and have at least a solubility for the reactants and the intermediate fluoroalkoxide formed between the acyl fluoride or ketone compound and the catalyst. Whether or not the products are significantly soluble in the solvent is a matter of choice and can be used as a controlling factor for selectively controlling the n value in the final product. For example, if a high n value is desired, it is advantageous that the product having at least n=0 to 1 be soluble in the solvent to give the intermediates (n=0 and n=1) times to react to produce the final n=1, 2 or higher product. In addition, the amount of solvent can be adjusted to accomplish somewhat similar results. Generally, when the ratio of the weight of solvent to the weight of the acid fluoride is from about 0.3:1 to about 0.8:1, formation of the n=0 product is maximized. As the weight ratio increases, higher n values are obtained. Although there is no theoretical maximum amount of solvent which may be used, one may quickly determine the weight ratio to be used depending upon the value of the n that he desires. Suitable solvents which may be employed to take advantage of the solubility plus amount factor are tetraglyme, diglyme, glyme, acetonitrile, nitrobenzene and the like. Exemplary of a preferred solvent is tetraglyme which has a suitable solvency for the intermediate, but in a weight to weight ratio has limited solubility for the product n=0 and therefore can be used advantageously to precipitate the n=0 product (remove it from the reaction media), effectively controlling (minimizing) the production of higher n values, yet if higher n values are desired, greater quantities of the solvent can be employed to dissolve the product n=0 or an amount sufficient to maintain a quantity thereof in the reaction medium to permit the epoxide to further react with the n=0 product to produce higher n value products. By controlling the amount, again it is possible to salt-out the intermediate n-values as a function of their solubility and quantity in the solvent-reaction media.

In a somewhat similar manner, the catalyst amount functions as a control of the end product n value. While the source of the fluoride ion is not critical, the amount of catalyst will to a significant measure establish the reactivity of the acid fluoride and thus determine the rate of reaction of the acid fluoride with the epoxide. Significant amounts of the catalyst, up to stoichiometric amounts based on the acid fluoride or ketone, will favor epoxide reacting on the feed acid fluoride. Whereas lesser catalytic amounts, with respect to the acid fluoride will favor the reaction of the epoxide with the n=0 acid fluoride product forming higher n products. As has been noted, substantially any fluoride ionizable at the reaction conditions may be used as a catalyst, however, CsF and KF are the most preferred but AgF, tetra alkyl ammonium fluoride as well as others listed by Evans, et al., *J. Org. Chem.* 33 1837 (1968) may be employed with satisfactory results.

The temperature of the reaction also effectuates a controlling factor on the end product obtained. For example, low temperatures such as $-20°$ C. favor n=0 products and higher temperatures, 50° C. and above, favor higher n values.

In summary, the following table illustrates the effect each parameter of the reaction has on the n value of the final product.

|  | n = 0 | n = 12 |
|---|---|---|
| Ratio of ketone or acyl fluoride to epoxide | 3/1 | 1/20 |
| Solvent amt. | small | large |
| Temp. | low | high |
| Catalyst | high | low |

EXAMPLES

EXAMPLE 1

90 ml of dry tetraglyme and 39.5 gms of anhydrous CsF were added to a 500 ml 3-neck flask equipped with a stirrer, thermometer, $-78°$ C. reflux condenser, and an inlet port. Downstream of the reactor were $-78°$ C. and liquid $N_2$ cold traps. A slight back pressure was maintained on the system with dry $N_2$.

The reactor was cooled to 0° C. to 5° C. and 126 grams of fluorosulfonyldifluoroacetylfluoride

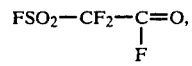

were added slowly over a 20 minute period and then allowed to mix for another 20–30 minutes to ensure formation of the alkoxide.

64.3 grams of

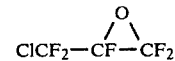

were added slowly over an hour and 45 hours while maintaining the reactor temperature at 0° to 5° C. After the epoxide addition, the contents were allowed to mix for an additional hour. The temperature was allowed to rise to room temperature. When stirring ceased, two separate layers formed. The bottom layer was drawn off and weighed 104.7 grams. VPC analysis of this product showed 92% n=0 product and 7.85% lights or product formed by reaction of the epoxide with itself.

Conversion of the epoxide was essentially complete. Yield of epoxide to the n=0 product was 75.3%.

The products were analyzed further by GC-MS and the following compounds were identified:

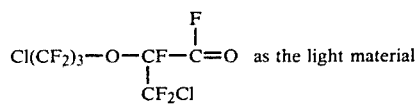 as the light material

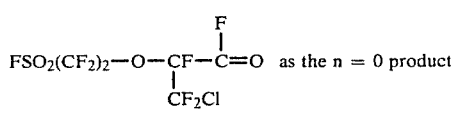 as the n = 0 product

Products were analyzed further by IR. The —COF groups present at 1870–1880 wave no., —$FSO_2$ group at 1460 and 1240 wave nos.; and —SF at 810 wave number for n=0 product.

The products had retention times of 1.35 and 2.74 minutes, respectively, on a VPC using six feet columns of 20% viton on Celite. Column temperature of 60° C.

EXAMPLE 2

35 ml of dry tetraglyme and 15.6 gms CsF were added to a 3-neck 100 ml flask equipped with a stirrer, thermometer, −78° C. reflux condenser and an inlet port. Downstream of the reactor were two −78° C. cold traps in series. A slight back pressure was maintained with dry $N_2$. Tetraglyme and CsF were mixed for 45 min. to 1 hour.

The reactor was cooled to 0° C. to 5° C. and 49.32 grams of fluorosulfonyl difluoro acetyl fluoride

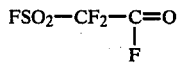

were added slowly over a 20 minute period, allowed to mix at 0° to 5° C. for 2 hours and then the temperature was raised slowly to room temperature to ensure the formation of the alkoxide. After cooling the reactor to 0° C., 25 grams of chloropentafluoropropylene oxide,

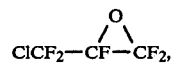

were added slowly over a 3-4 hour period. After the epoxide addition was complete, the contents were mixed for an additional hour. The temperature was allowed to rise to room temperature. When stirring was stopped, two liquid phases separated. 38.94 gms of the heavy or bottom layer was collected. Analyses by VPC showed 87.86% of n=0 product, 5% unreacted reactants, and 4.2% of a higher molecular wt. product. This gave an essentially complete conversion of the epoxide and a 68.9% yield of epoxide to the n=0 product.

The unreacted reactant ($FSO_2CF_2CFO$) was distilled off the product.

35 ml of tetraglyme and 8 grams CsF were mixed for 40 minutes. The heavies from the above distillation were added slowly over a 20 minute period and mixed for 1 hour at 0° C. to 5° C. The reactor was warmed to room temperature to ensure formation of the alkoxide. After cooling again to 0° C. to 5° C., 19.6 grams of

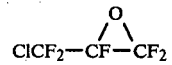

were added slowly over a 2-3 hour period, and then allowed to mix at 0° C. to 5° C. for another hour. The reactor was warmed to room temperature. After stirring was stopped, two separate layers formed. 35.67 grams of bottom or product layer was collected. Analyses by VPC showed 12.8% n=0 product, 57.4% n=1, and 6.8% n=2 product. Thus, of the n=0 product that reacted, 45.9% was converted to the n=1 product.

The following products were identified by mass spectrometer:

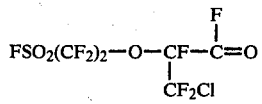

-continued

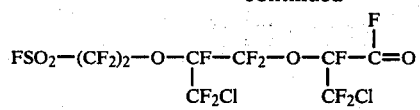

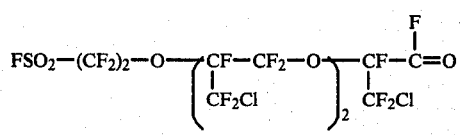

Mass spectroscopy fragmentation pattern reported consistent with this structure of n=2.

The infrared showed the characteristic $SO_2F$ and

bands, VPC retention times using the column described in Example 1 with a temperature program of 4 min. at 60° C., followed by a rise to 220° C. at 16°/min. were 2.72, 5.74, 8.18, respectively.

EXAMPLE 3

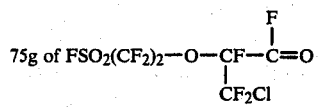

was added dropwise to a 500 ml vessel containing 200 g tetraglyme and 15.2 g CsF. The vessel was fitted with a cold finger condenser and two traps on the effluent; one dry ice acetone and the other liquid nitrogen. The acid fluoride was stirred for one hour after the addition was completed and then

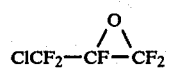

was added at a rate such that no reflux was observed on the cold finger. A total of 18.3 g was added, keeping the temperature below 35° C. After completing the addition, the mixture was stirred for an hour. The vessel contents were poured into a separatory funnel under dry nitrogen blanket and the lower product layer was allowed to settle out. The product layer was drained off and analyzed chromatographically as: 1 part n=3, 1.1 parts n=2, 12 parts n=1, 4.6 parts residual n=0.

EXAMPLE 4

30 ml of dry tetraglyme and 14.15 gms (0.0932 mole) CsF were added to a 100 ml 3-neck flask equipped with a stirrer, thermometer, −78° C. reflux condenser, and an inlet port. Downstream of the reactor were two −78° C. cold traps in series. A slight back pressure was maintained on the system with dry $N_2$. Tetraglyme and CsF were mixed for at least 45 minutes.

The reactor was cooled to −20° C. and 16.83 grams (0.093 moles) of

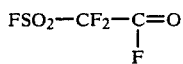

added. The temperature was brought up to 20°–25° C. and 30.2 gms of

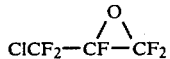

were added in increments of 2 to 3 grams over a 4 hour period while maintaining the reactor at 25°–28° C. After the epoxide addition, the contents were stirred for an additional 1.5 hours. When stirring ceased, two separate layers formed and were separated with a separatory funnel. 28 grams of product (bottom layer) were collected. Analysis by VPC showed 13.4% n=0 product, 33.8% n=1 product, and 4.3% n=2 product. In addition, there were products (dimers and trimers) of the epoxide.

Products were analyzed further by GCMS and the following compounds were identified:

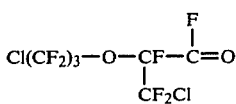

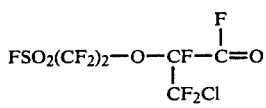

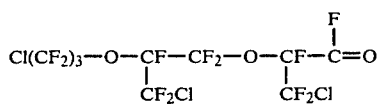

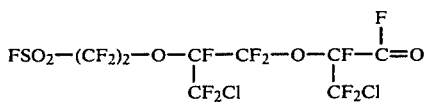

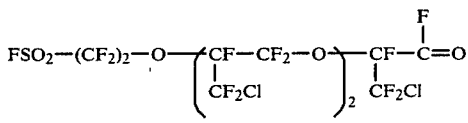

EXAMPLE 5

200 ml of dry tetraglyme and 15.19 gms (0.10 moles) of CsF were added to a 500 ml 3-neck flask equipped with a stirrer, thermometer, −78° C. reflux condenser, and an inlet port. Two −78° C. cold traps in series were located downstream of the reflux condenser. A slight back pressure was maintained on the system with dry $N_2$. After stirring for 1 hour, the reactor was cooled to −5° C., and 51.22 gms (0.20 moles) of methyl perfluoroglutaryl fluoride

were added dropwise. Reactor was stirred overnight at room temperature. Reactor was cooled to −5° C. and 18.25 gms (0.10 moles) of chloropentafluoro propylene oxide

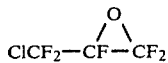

were added slowly. After the epoxide addition was complete, samples were taken after 30 min. and 1.5 hr. and analyzed by VPC. Temperature was then raised to room temperature over one hour period and sample analyzed by VPC.

The products were distilled out of the reactor under 30″ vacuum while heating to 160° C. Overhead temperature was 65° C. at this point. 49.38 gms collected in first cold trap and 2.5 grams collected in the second trap. Products were analyzed by VPC.

The material caught in the first cold trap was distilled in a microcolumn to remove the unreacted methylperfluoroglutaryl fluoride. All material boiling up to 145° C. was removed in this manner. Everything heavier was retained in the pot. Wt. was 18.44 grams. Heavies were analyzed by VPC, mass spectroscopy and I.R.

Peaks on the VPC were 7.21, 7.62, 8.86, and 10.47 minutes. Mass spectroscopy showed that the 7.21 peak had the structure

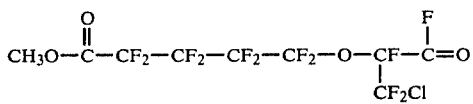

and the 8.86 peak the structure

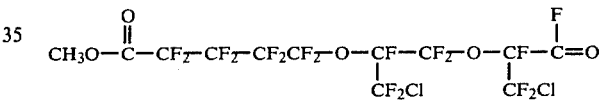

IR showed bands at 2960, 1860, 1770–1780 $Cm^1$.
The 1860 $Cm^{-1}$ band is the —COF group and the 1770–1780 $Cm^{-1}$ is the ester $-\overset{\overset{O}{\|}}{C}-$ group. The 2960 $Cm^{-1}$ is due to the $CH_3$ group.

EXAMPLE 6

25 ml of tetraglyme and 6.9 gms of CsF were added to a 50 ml 3 neck flask equipped with stirring bar, thermometer, reflux condenser, and an inlet port. Two −78° C. cold traps in series were located downstream of the reflux condenser. A slight backpressure was maintained on the system with dry $N_2$. The tetraglyme and CsF were allowed to mix for 1 hour at room temperature, lowered to 10° C.–20° C., and 48 grams of $FSO_2CF_2CFO$ were added and allowed to mix for 1 hour. Mixture was cooled to 0° C. and 25 grams of

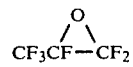

were added over an hour and 20 minute period, while maintaining a temperature of 0° C. to 10° C. After mixing at this temperature for 2 hours, the temperature was increased to room temperature. The product was separated as a clear, dense, bottom layer. 50.5 grams were recovered which was determined to be 80.16%

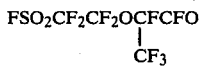

by VPC analysis.

The lower boiling components were removed leaving a mixture containing 88.6% of the desired acid fluoride. 5 ml of tetraglyme and 1.7 gms CsF were added to a 50 ml 3 neck flask equipped as above and the mixture was stirred for 30 minutes. 5 grams of distilled

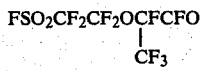

were added and mixed at 10°–20° C. for 1 hour. 1.4 gms of

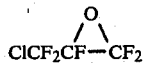

were added while maintaining a temperature of 0° to 10° C., and held at this temperature for 1 hour. Temperature was increased to room temperature, 5 ml of tetraglyme added, and the product separated from the solvent. 3.0 grams of product were obtained and analyzed as 63.98%

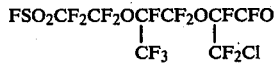

having a 6.47 minute retention on the VPC and confirmed by I.R. and mass spectroscopy.

What is claimed is:

1. As a composition of matter the compounds represented by the general formula:

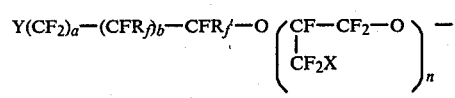

-continued

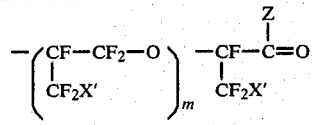

where
 a = an integer from, and including, 0 to 3;
 b = an integer from, and including, 0 to 3;
 m = an integer from, and including 0 to 6;
 n = an integer from and including 0 to 6;
 $R_f$ and $R_f'$ are each independently selected from the group consisting of F, Cl, perfluoroalkyl and fluorochloroalkyl;
 X = F, Cl, Br, or mixtures thereof when n > 1;
 X' = Cl, Br, or mixtures thereof;
 Y is selected from the group consisting of

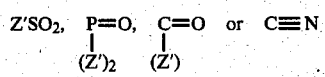

Z' is F, Cl, Br, OH, NRR' or OA
 R and R' are independently selected from the group consisting of hydrogen, an alkyl having one or more than one carbon atom and an aryl;
 Z = F, Cl, Br, OH, NRR' or OA;
 R and R' are independently selected from the group consisting of hydrogen, an alkyl having one or more carbon atom and aryl;
 A = alkali metal, quaterary ammonium or R.

2. The compounds of claim 1 where X = Cl.
3. The compounds of claim 1 where X' = Cl.
4. The compounds of claim 1 where X = F and n is 1–6.
5. The compounds of claim 1 where X = F and X' = Cl.
6. The compounds of claim 1 where Y = Z'SO$_2$.
7. The compounds of claim 1 where Y = COZ'.
8. The compounds of claims 6 or 7 where X = Cl.
9. The compounds of claims 6 or 7 where X' = Cl.
10. The compounds of claims 6 or 7 where X = Cl and X' = Cl.
11. The compounds of claims 1, 3, 6 and 7 where n = 0.
12. The compounds of claims 1, 2, 3, 4, 5, 6 and 7 where m = 0.
13. The compounds of claim 1 where n = 0 and m = 0.
14. The compounds of claim 13 where X' = Cl.
15. The compounds of claim 1 where n = 1 and m = 0.
16. The compounds of claim 15 where X = Cl.
17. The compounds of claim 16 where X' = Cl.

* * * * *

UNITED STATES PATENT AND TRADEMARK OFFICE
CERTIFICATE OF CORRECTION

PATENT NO. : 4,337,211
DATED : June 29, 1982
INVENTOR(S) : Bobby R. Ezzell, et al.

It is certified that error appears in the above—identified patent and that said Letters Patent is hereby corrected as shown below:

Col. 1, line 33, add --a-- in front of radical.

Col. 2, line 68, delete "grater" and insert --greater--.

Col. 7, line 5, delete "N2-12" and insert --n=2-12--.

Col. 7, line 18, delete "times" and insert --time--.

Col. 8, line 41, delete "45 hours" and insert --45 minutes--.

Col. 14, in the formula, line 4, delete "$CF-CF_2-O$" and insert --$CF-CF_2O$--.

Col. 14, line 32, delete "quaterary" and insert --quaternary--.

Signed and Sealed this

First Day of February 1983

[SEAL]

Attest:

GERALD J. MOSSINGHOFF

Attesting Officer    Commissioner of Patents and Trademarks